United States Patent [19]

Hughes

[11] 4,087,472
[45] May 2, 1978

[54] ISOMERIZATION PROCESS

[75] Inventor: William B. Hughes, Bartlesville, Okla.

[73] Assignee: Phillips Petroleum Company, Bartlesville, Okla.

[21] Appl. No.: 714,932

[22] Filed: Aug. 16, 1976

[51] Int. Cl.$^2$ ............................................. C07C 29/00
[52] U.S. Cl. ................................ 568/906; 260/601 R; 260/666 PY; 260/683.2; 568/822; 568/807; 568/813; 568/838; 568/821; 568/825
[58] Field of Search ........................ 260/642 A, 601 R

[56] References Cited

U.S. PATENT DOCUMENTS 3,148,224  9/1964  Luttinger ............................. 260/666

Primary Examiner—Joseph E. Evans

[57] ABSTRACT

An olefinic hydrocarbon is isomerized utilizing a catalyst system consisting essentially of a mixture of a nickel complex of the formula $(R_3P)_2NiX_2$ and an alkali metal borohydride.

9 Claims, No Drawings

ISOMERIZATION PROCESS

This invention relates to a process for the isomerization of an isomerizable olefinic compound.

Various processes are known for isomerizing olefinic compounds; however, such processes are, in general, limited in scope and additionally, suffer from one or more limitations such as unfavorable equilibrium conditions, excessive cracking of the olefinic compound, undesirable polymerization of the olefinic compound, and the like.

It is an object of the present invention to provide a novel process for isomerizing an isomerizable olefinic compound.

Other objects and advantages of the invention will become apparent from the following description and appended claims.

In accordance with the present invention there is provided a process for isomerizing isomerizable olefinic compounds which comprises contacting such compounds in the liquid phase with a catalyst consisting essentially of a mixture of a nickel complex represented by the formula $$(R_3P)_2NiX_2$$

wherein X is a halogen selected from the group consisting of chlorine, bromine and iodine, and R is a hydrocarbon radical having from 1 to 10 carbon atoms, and an alkali metal borohydride represented by the formula $$MBH_3Z$$

wherein M is an alkali metal selected from the group consisting of lithium, sodium and potassium, and Z is —H or —CN.

Examples of suitable nickel complex compounds of the above general formula include bis(triethylphosphine)dichloronickel, bis(triphenylphosphine)dichloronickel, bis(trimethylphosphine)dibromonickel, bis(trihexylphosphine)diiodonickel, bis(tridecylphosphine)dichloronickel, bis(tribenzylphosphine)dibromonickel, bis(tri-[4-butylphenyl]phosphine)dichloronickel, bis(tributylphosphine)dibromonickel, bis(tricyclopentylphosphine)diiodonickel, bis[tri(4-tolyl)phosphine]dibromonickel, bis(tricyclohexylphosphine)dibromonickel, and the like. The above-described nickel (II) complexes of triorganophosphines and halogens are well known in the art and methods for their preparation are known to those skilled in the art.

Examples of suitable alkali metal borohydrides or alkali metal cyanoborohydrides which can be used in the instant invention include lithium borohydride, sodium borohydride, potassium borohydride, lithium cyanoborohydride, sodium cyanoborohydride and potassium cyanoborohydride. As subsequently used herein and in the claims, the terms "borohydride compound" or "borohydride" are used generically to include both the borohydride and cyanoborohydride compounds.

The catalyst system of the present invention consists essentially of a mixture of the nickel complex compound and the borohydride compound. The components are utilized in a molar ratio of borohydride compound to the nickel complex component in a range of from 0.5:1 to 5:1, preferably from 1:1 to 2:1.

The amount of catalyst system utilized in the isomerization process of the present invention can range from about 1,000 moles of reactant per mole of the nickel complex compound to 1 mole of reactant per mole of nickel complex compound.

In an embodiment of the present invention, the nickel component of the isomerization catalyst system can be anchored to a polymeric substrate through the organophosphine ligand of the complex. Such procedures have been recently described in the art and certain of the phosphine ligand polymeric anchor materials are commercially available, such as polymer-bound triphenylphosphine on styrene-divinyl benzene copolymers of varying degrees of cross-linking. As disclosed in the recent art in this area, the use of such polymeranchored catalytic components enables the practice of typical heterogeneous catalyst techniques for the typical homogeneous catalyst systems, such as for example, a continuous process or ease of catalyst recovery. If this embodiment is utilized, the above-described ratio ranges can be expressed in terms of moles of borohydride per gram equivalent of nickel and moles of reactant per gram equivalent of nickel.

The process of this invention is applicable to the isomerization of isomerizable olefinic hydrocarbons and olefinic alcohols having 4 to 20 carbon atoms and at least one migratable ethylenic bond per molecule. The term "migratable ethylenic bond" is intended to mean an ethylenic bond, i.e., $$>C=C<$$

which is bonded in the compound to a carbon atom in the alpha position to the ethylenic bond, which alpha carbon atom bears at least one hydrogen atom. The ethylenically unsaturated compounds most favorably employed herein contain at least 1 migratable ethylenic bond which is an isomerizable bond, i.e., an ethylenic bond which is not present in its most thermodynamically favored position in the ethylenically unsaturated molecule. Similarly, compounds containing one or more migratable ethylenic bonds are referred to herein as "isomerizable compounds". It is preferred that in compounds having more than one ethylenic bond, the bonds be in a non-conjugated relationship.

The ethylenically unsaturated compounds which are contemplated for use in the present invention include the isomerizable acyclic hydrocarbons, alicyclic olefinic compounds wherein the ethylenic bond is exocyclic to the carbocyclic ring, within the ring or attached to the carbocyclic ring, and isomerizable olefinic alcohols. These isomerizable compounds can be substituted with aryl radicals. Compounds having acetylenic unsaturation are believed to be unsuitable for use in the instant invention. Some specific examples of isomerizable olefinic hydrocarbon compounds include: 1-butene, 1-pentene, 1-octene, 1-dodecene, 1-eicosene, 2-heptene, 2-decane, 2-octadecene, 3-methylcyclohexene, 1,5-cyclooctadiene, 1,5,9-cyclododecatriene, bicyclo[4.3.0]nona-3,6-diene, bicyclo[4.3.0]nona-3,7-diene, 4-vinylcyclohexene, 5-vinyl-2-norbornene, limonene, 1,13-tetradecadiene, 3-methyl-1-butene, 2,4,4-trimethyl-1-pentene.

Some specific examples of isomerizable olefinic alcohols include: 3-buten-2-ol, 3-buten-1-ol, 3-methyl-3-buten-2-ol, 3-methyl-3-buten-1-ol, 3-penten-2-ol, 5-ethyl-6-nonen-4-ol, 2-methyl-7-butyl-4-tridecen-6-ol, 2-methyl-4-isopropyl-5-dodecen-3-ol, 11-eicosen-10-ol, 1-cyclohexyl-5-cyclopentyl-3-penten-1-ol, 1-phenyl-4-p-tolyl-3-buten-2-ol, 3-benzyl-4-methyl-5-hexen-3-ol, 3-methylene-1-undecanol, 5-methylene-6-methyl-6-tetradecanol, 4-hexen-1-ol, 5-octen-2-ol, 2-m-tolyl-3-(3-methylcyclopentyl)-3-buten-1-ol, 2-cyclopenten-1-ol, 3-cyclohexen-1-ol, 5-ethyl-8-phenyl-2-cycloocten-1-ol, 3-cyclododecen-1-ol, 2-cycloeicosen-1-ol, and the like.

The isomerization process of the instant invention utilizing the catalyst system previously described is carried out over a temperature range of about 0° C to about 150° C, preferably from 25° to 100° C.

The time employed for the isomerization reaction can vary over a wide range depending upon the temperature, catalyst activity and amount and reactivity of the starting material, but will generally be within the range of about 10 minutes up to 48 hours. The particular time employed for the isomerization reaction can be readily determined by the rate at which the isomerization mixture approaches the equilibrium composition for the reaction mixture.

The isomerization process of the instant invention is carried out at a pressure sufficient to maintain the reactants and products substantially in the liquid phase under the temperature employed. The reaction can be carried out in the presence of an inert gas, such as nitrogen, helium or argon. The term "inert gas" is intended to mean a gas which will not react with the isomerizable compounds under the conditions of the present process. Hydrogen, for example, would not be a suitable gas.

A reaction diluent is not required for the instant process, however, the use of such diluent is presently preferred. Typical diluents that can be used include lower saturated alcohols hving from 1 to 4 carbon atoms per molecule and chlorobenzene. The amount of diluent employed will generally be in the range of from 1 to 100 parts by volume per 100 parts by volume of reactent. The reactant, catalyst components and diluent for the instant process can be charged to the reaction vessel in any order, however, it is presently preferred to avoid separate contact of the alkali metal borohydride and the olefinic alcohol reactant for any significant length of time. A preferred charge order is: diluent, if utilized, nickel complex component, borohydride compound, and reactant.

The reaction mixture obtained upon isomerization of the olefinic compound according to the instant invention can generally be treated by first, filtration when appropriate, then a fractional distillation to separate the components of the reaction mixture. Other separation methods can also be utilized when appropriate, such as fractional crystallization or macroscale chromatography technique.

The isomerization process of the instant invention can be utilized for the conversion of less valuable compounds to those having greater value. For example, the compound 5-ethylidene-2-norbornene is utilized as a termonomer in the preparation of elastomeric copolymers of ethylene, propylene and a diene such as 5-ethylidene-2-norbornene. These polymers are well known in the art and have become increasingly commercially significant within the last several years. The isomerization process of the present invention provides a method for converting 5-vinyl-2-norbornene to the 5-ethylidene-2-norbornene. Additionally, 3-buten-1-ol, which can be made from propylene and formaldehyde, can be isomerized to butyraldehyde, a useful compound in many respects such as conversion to 2-ethylhexanol, a widely used solvent and plasticizer component.

The following examples illustrate the invention:

EXAMPLE I

A Diels-Alder tube was charged with 0.18 gram of bis(triethylphosphine)dichloronickel, 0.1 gram of sodium cyanoborohydride, and 0.6 gram of 3-buten-1-ol. Charging of the above reaction mixture was carried out under nitrogen. Immediately upon adding the unsaturated alcohol, the dark red nickel complex became yellow. The reaction mixture was heated at 80° C for three hours. At the end of this time, the reaction mixture was analyzed by gas-liquid phase chromatography which indicated the presence of cis- and trans-crotyl alcohol (2-buten-1-ol) as well as butyraldehyde. The above result demonstrates operability of the catalyst system of the instant invention for isomerization of an olefinic alcohol to another olefinic alcohol and a carbonyl compound.

EXAMPLE II

In a manner similar to that utilized in Example I above, a Diels-Alder tube was charged with 0.19 gram of bis(tribenzylphosphine)dichloronickel, 0.05 gram of sodium cyanoborohydride, and 0.6 gram of 3-buten-1-ol. The dark red nickel complex slowly turned yellow. The reaction mixture was stirred at room temperature for 1.33 hours and then 0.6 gram of additional 3-butene-1-ol was added. The reaction mixture was stirred for 3 hours and then allowed to stand for about 16½ hours. Analysis by gas-liquid phase chromatography of the reaction mixture showed the presence of cis- and trans-crotyl alcohol and butyraldehyde. The result of this run again demonstrates operability for a catalyst system of the instant invention for the conversion of an olefinic alcohol to an isomeric olefinic alcohol and a carbonyl compound.

EXAMPLE III

A Diels-Alder tube was charged with 0.19 gram of bis(tribenzylphosphine)dichloronickel, 0.05 gram of sodium cyanoborohydride, and 0.5 ml of absolute ethanol. The mixture was stirred at room temperature for 0.5 hour. The red nickel complex had become yellow. To the above mixture, 2.0 ml of 1-pentene was added. Analysis of the reaction mixture by gas-liquid phase chromatography after 1.5 hours indicated predominantly cis- and trans-2-pentene were present in the reaction mixture. The reaction mixture was reanalyzed after standing overnight (about 16 hours). The latter analysis gave the following composition for the olefinic hydrocarbon: 2.3 weight percent 1-pentene, 58.2 weight percent trans-2-pentene, and 38.3 weight percent cis-2-pentene. Results of this run demonstrate operability of the catalyst system of the instant invention for isomerization of an olefinic hydrocarbon to other isomeric olefinic hydrocarbons.

EXAMPLE IV

A Diels-Alder tube was charged with 0.19 gram of bis(tribenzylphosphine)dichloronickel, 0.05 gram of sodium cyanoborohydride, and 0.5 ml of absolute ethanol. After 0.5 hour at room temperature, the reaction mixture was charged with 2 ml of 5-vinyl-2-norbornene. After 5 hours total reaction time, 5 ml of chlorobenzene was added to the reaction mixture. The reaction mixture was allowed to stand over the weekend (about 60 hours), then heated at 80° C for two hours. Analysis of the reaction mixture by gas-liquid phase chromatography indicated the presence of 5-ethylidene-2-norbornene. The result of the above described run demonstrates the operability of the catalyst system of the instant invention for the isomerization of a diolefinic hydrocarbon to an isomeric diolefinic hydrocarbon.

Each of the isomerization reactions in Examples I through IV was carried out under a nitrogen atmosphere.

Reasonable variations and modifications, which will be apparent to those skilled in the art, can be made in this invention without departing from the spirit and scope thereof.

What is claimed is:

1. A process for isomerizing an isomerizable olefinic alcohol having from 4 to 20 carbon atoms per molecule and at least one ethylenic bond which comprises contacting said olefinic alcohol in the liquid phase under isomerization conditions with a catalyst consisting essentially of a mixture of a nickel complex represented by the formula $$(R_3P)_2NiX_2$$

wherein X is a halogen selected from the group consisting of chlorine, bromine and iodine, and R is a hydrocarbon radical having from 1 to 10 carbon atoms, and an alkali metal borohydride represented by the formula $$MBH_3Z$$

wherein M is an alkali metal selected from the group consisting of lithium, sodium and potassium, and Z is —H or —CN.

2. The process of claim 1 wherein said olefinic alcohol is 3-buten-1-ol.

3. The process of claim 1 wherein the molar ratio of said borohydride to said nickel complex is in the approximate range of 0.5:1 to 5:1.

4. The process of claim 1 wherein said catalyst system is employed in an amount ranging from 1 to 1000 moles of said olefinic alcohol per mole of said nickel complex.

5. The process of claim 1 wherein said isomerization is carried out by contacting said olefinic alcohol with said catalyst system at a temperature in the approximate range of 0° to 150° C.

6. The process of claim 1 wherein said isomerization is carried out at a pressure sufficient to maintain said olefinic alcohol reactant and the resulting product in the liquid phase at reaction temperature.

7. The process of claim 1 wherein said isomerization is carried out in an inert reaction diluent.

8. The process of claim 1 wherein said nickel complex is bis(triethylphosphine)dichloronickel and said borohydride is sodium cyanoborohyddride.

9. The process of claim 1 wherein said nickle complex is bis(tribenzylphosphine)dichloronickel and said borohydride is sodium cyanoborohydride.

* * * * *